US006323380B1

(12) United States Patent
Lockhart et al.

(10) Patent No.: US 6,323,380 B1
(45) Date of Patent: Nov. 27, 2001

(54) WATER REMOVAL IN PURIFICATION OF VINYL CHLORIDE

(75) Inventors: Wayne A. Lockhart, Sherwood Park; Terrence M. Nimchuk, Lamont; Joseph J. D. Brochu, Gibbons; Ralph Smeding, Saint Albert, all of (CA)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/553,509

(22) Filed: Apr. 20, 2000

Related U.S. Application Data
(60) Provisional application No. 60/130,787, filed on Apr. 23, 1999.

(51) Int. Cl.$^7$ .................................................. C07C 17/42
(52) U.S. Cl. ............................................................ 570/262
(58) Field of Search ............................................. 570/262

(56) References Cited

U.S. PATENT DOCUMENTS

| | | |
|---|---|---|
| 3,216,178 | 11/1965 | Sauty . |
| 3,267,644 | 8/1966 | Jacobowsky . |
| 3,275,549 | 9/1966 | Crabb et al. . |
| 3,948,622 | 4/1976 | Tsao . |
| 4,008,289 | 2/1977 | Ward et al. . |
| 4,133,663 | 1/1979 | Skinner . |
| 4,286,390 | 9/1981 | Convers et al. . |
| 4,287,089 | 9/1981 | Convers et al. . |
| 4,418,233 | 11/1983 | Danz et al. . |
| 4,642,400 | 2/1987 | Cowfer et al. . |
| 4,663,052 | 5/1987 | Sherman et al. . |
| 5,198,121 * | 3/1993 | Masini ................................ 570/262 |
| 5,436,378 | 7/1995 | Masini et al. . |
| 5,507,920 | 4/1996 | Schwarzmaier et al. . |

FOREIGN PATENT DOCUMENTS 2 054 574 A    2/1981 (GB) .

OTHER PUBLICATIONS

"Vinyl chloride monomer prepn.—using crude sepn. distn. step," Derwent 97–163342/15 and related article "Use of a Crude Separation Distillation Step in the production of Vinyl Chloride Monomer", 39405, Research Disclosure, Jan. 1997, pp. 78–79.
Chemical Abstract, 95:116187g, "Process for the preparation of vinyl chloride", Brit. 2,054,574 (Feb. 1981).
Chemical Abstract, 101:130210h, "Drying of chlorohydrocarbons", Ger. 209,182 (Apr. 25, 1984).
Chemical Abstract, 116:129861z, "Thermal treatment of 1,2–dichloroethane fractions for vinyl chloride production", Ger. 296,271 (Nov. 28, 1991).
Chemical Abstract, 116:129862a, "Thermal treatment of 1,2–dichloroethane fractions for vinyl chloride production" Ger. 296,270 (Nov. 28, 1991).

* cited by examiner

*Primary Examiner*—Alan Siegel
(74) *Attorney, Agent, or Firm*—Dale H. Schultz

(57) ABSTRACT

Removal of water in a vinyl chloride monomer purification system is achieved through (1) providing a distillation column for separation of a liquid admixture of vinyl chloride, hydrogen chloride, and water into (a) an essentially pure vinyl chloride product stream and (b) a hydrogen chloride distillate stream; and (2) placing a drying system in fluid communication with the distillation column midsection at a connection point where the water is at sufficient concentration to provide a useful mass transfer flux of water from a withdrawn midsection stream into a drying agent.

8 Claims, 3 Drawing Sheets

WATER REMOVAL IN PURIFICATION OF VINYL CHLORIDE

CROSS-REFERENCE TO PRIOR APPLICATION

This Application claims the benefit of U.S. Provisional Application No. 60/130,787 filed on Apr. 23, 1999.

FIELD OF THE INVENTION

This invention relates to the purification of Vinyl Chloride Monomer and the removal of water in Vinyl Chloride Monomer finishing.

BACKGROUND OF THE INVENTION

In purifying Vinyl Chloride Monomer (VCM) produced by the cracking of 1,2 dichloroethane (EDC) according to well-known commercial manufacturing processes, trace amounts of water must be handled. This trace water either (a) is formed in the cracking process, (b) results from small amounts of water present in the EDC fed to the cracking furnaces used in the cracking process, or (c) is formed in-situ within the distillation process. Hydrochloric acid (HCl) is formed as a by-product or co-product in the production of VCM from EDC; and this HCl, when mixed with water, forms a mildly corrosive mixture. However, when the overall water concentration exceeds the solubility limit of water in VCM, the VCM becomes saturated and the water enters into a free phase state in HCl; this separate free-water phase is highly corrosive in comparison to the phase where the water concentration is below the saturation limit for VCM.

A drying operation can be used to remove water from an admixture of vinyl chloride, HCl, and water where the vinyl chloride is present either in substance or in trace quantity. One such drying system is described in U.S. Pat. No. 5,507,920 entitled "Process And Apparatus For Purifying Vinyl Chloride, which issued to P. Schwarzmaier, P. Kammerhofer, M. Stöger, H. Kalliwoda, and I. Mielke on Apr. 16, 1996. This patent describes both the use of an evaporator and an optional molecular sieve or silica gel desiccant in drying water from a stream of HCl, water, and entrained vinyl chloride which has been distilled away (as an overhead vapor stream from a HCl/VCM distillation column, the third distillation column in a three column vinyl chloride separation system) from a feed stream rich in vinyl chloride and also containing HCl and entrained water. The patent describes that "the greatest water concentration prevails at the top of" the third HCl/VCM distillation column in that three column vinyl chloride separation system and that, accordingly, the "drying" system is installed at the beginning of the vapor line recycling HCl and entrained vinyl chloride to the feed stream of the first distillation column of that three column vinyl chloride separation system.

The insertion of a drying system in the output vapor stream of a process line has some drawbacks, however. Any breakdown or plugging of such a drying system can rapidly affect the fluid dynamics in the HCl/VCM distillation column generating the vapor stream. Also, vapor streams tend to need physically larger equipment than liquid streams where the same mass of material is being handled; and, respective to the larger equipment, it requires more capital to install a vapor handling system than a liquid system respective to handling of the same mass of material. The use of a liquefaction system for the vapor stream can effectively solve some of the above issues, but this also requires capital and a cooling system to remove heats of vaporization and superheating. A true solution to the issue of water removal, therefore, is to provide a drying system which (1) removes water rapidly and efficiently from the VCM purification system at a location having a relatively high water concentration, (2) does not impact or potentially adversely affect the fluid dynamics in the HCl/VCM distillation column, (3) provides for a safe operating environment, and (4) minimizes the amount of capital needed to effect acceptable water removal from the vinyl chloride monomer purification system. The present invention provides a solution to these needs.

SUMMARY OF THE INVENTION

The invention in summary provides a method of removing water in a vinyl chloride monomer purification system by steps comprising (1) providing a distillation column (having a top, a bottom, and a midsection) for separation of a liquid admixture of vinyl chloride, hydrogen chloride, and water into (a) an essentially pure vinyl chloride product stream and (b) a hydrogen chloride distillate stream; and (2) placing a drying system in fluid communication with the distillation column midsection at a location where the water is at sufficient concentration to provide a useful mass transfer flux of water from a withdrawn midsection stream into a drying agent.

DETAILED DESCRIPTION OF PREFERRED EMBODIMENTS

Figure 1:
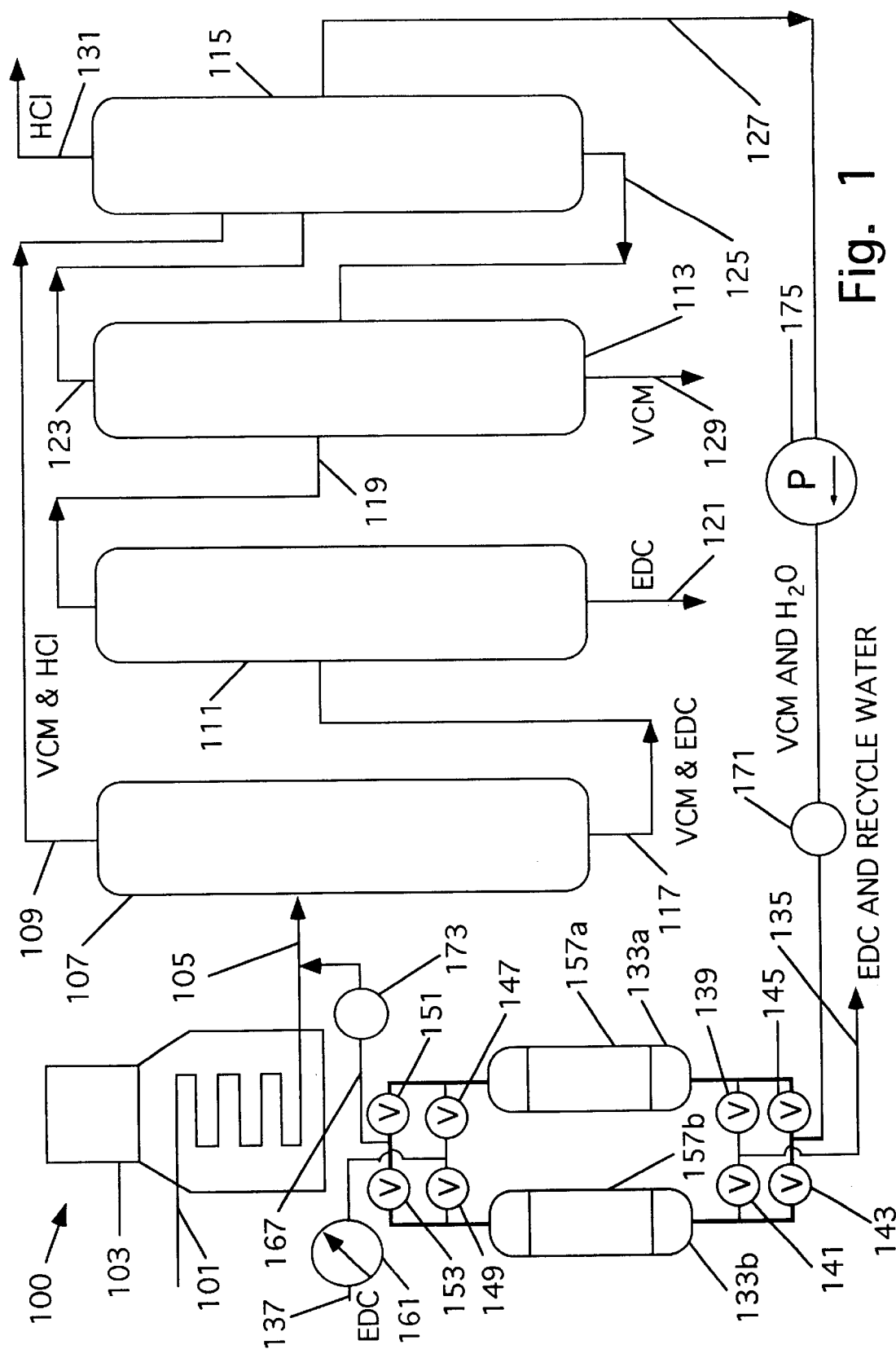
FIG. 1 shows a vinyl chloride purifying system equipped with a drier, in accord with a preferred embodiment of the present invention.

The physical properties of VCM/HCl/water mixtures are non-ideal and are difficult to model by conventional modeling techniques with commercially available databases; this difficulty has precluded accurate prediction and simulation of stagewise composition within a HCl/VCM distillation column, and it has accordingly been difficult to undertake any effective, focused measures to remedy corrosion problems associated with trace water from EDC cracking. The present invention derives from a surprising discovery that a certain amount of water is effectively concentrated and retained (dynamically "trapped") to define a "high water concentration zone" in the midsection of a HCl/VCM distillation column used to separate HCl from VCM in the purifying section of the Vinyl Chloride manufacturing facility according to FIG. 1. It is believed that the concentration of water is sufficiently high to establish conditions leading to at least occasional existence, in some parts of the high water concentration zone, of a first liquid phase having water in vinyl chloride (with dissolved HCl) and a second liquid phase of vinyl chloride and HCl in water. It is further believed that the second liquid phase of vinyl chloride and HCl in water effects relatively rapid corrosion of the metallic components used in the HCl/VCM distillation column and ultimately effects failure of the HCl/VCM distillation column in performing according to design. HCl/VCM distillation column metallic components are constructed of either iron (carbon steel) or nickel/copper alloy (where the nickel/ copper alloy has a small percentage of carbon, manganese, iron, sulfur, and silicon); Monel™ (trademark of Huntington Alloys, Inco Allys International, Inc.) nickel/copper alloys are of preferable consideration for use in the corrosive environment in the HCl/VCM distillation column. The various corrosion products accumulate on distillation unit trays and plug openings in those trays, deteriorating operational characteristics of the unit to a point where shutdown and cleaning of the VCM purifying system is needed; such a shutdown represents a loss of productivity.

The term "dry" can function as a verb and as an adjective. In rigorous use as an adjective, "dry" references a material free of water (or, in some contexts, free of liquid). As a verb, "dry" references removal of moisture from a material toward a "dry" or "dryer" state; as such, "drying" of a material references a process for removing water (or some other liquid if contextually appropriate) from a material even though a relatively benign amount of water might still be present in the "dried" material at the conclusion of the "drying" process. This latter meaning is the intended meaning of the terms "dry" and "drying" as used herein, so that the VCM product after "drying" by the process of the present invention can still be considered "dry" or "dried", though some of the trace water remains in the VCM product in relatively benign amounts. (The levels of water that can be considered "benign" from a corrosion perspective in a given set of circumstances will vary from one set of circumstances to another, depending on the design and materials of construction for equipment or apparatus with which the "dried" VCM product will come into contact, the prevailing temperatures and pressures in the apparatus or equipment, the length of time during which the VCM product will contact the apparatus or equipment at such temperatures and pressures, and so forth; but, as a general rule, those water contents characteristic of hydrogen chloride used in the oxychlorination step of the various known overall EDC/VCM manufacturing processes are to be considered "benign". Thus, for example, VCM product produced by the process of the present invention should certainly be considered as "dry" or "dried" with water contents, on a hydrogen chloride and water only basis, on the order of about 100 parts per million or less by weight or less, but the overall objective of the invention is that the corrosion effects of the VCM product and internal streams within the VCM purifying system should be materially and markedly decreased. In this regard, the VCM product should be dried to a sufficient extent whereby a corrosion rate below 10 mm/year is achieved in the HCl/VCM distillation column tray components.)

From the standpoint of a drying operation, it is generally easier and more economical to remove water from a first mixture having water at a "higher" concentration rather than from a second mixture having water at a "lower" concentration because of the higher mass transfer driving force in the case of the first mixture as compared to the second mixture. In the HCl/VCM distillation column used respective to the present invention in separating HCl from VCM in the purifying section of the Vinyl Chloride manufacturing facility, the mid-section of the HCl/VCM distillation column affords, via the surprising discovery of the "high water concentration zone" as noted earlier, an opportunity for economically and effectively removing water from the VCM product without at the same time incurring the capital outlay and operational concerns discussed respective to the system described in the '920, Schwarzmaier et al. patent referenced above. The discovered "high water concentration zone" therefore provides a basis for a useful mass transfer flux of water from a withdrawn midsection stream into a drying agent.

It has been determined that silica gel is a suitable drying agent in this application. While silica gel has only limited water adsorption capability at process temperatures above 25 degrees C, silica gel is effective at drying VCM where the temperature is below about 25 degrees C. The mid-section of the HCl/VCM distillation column (where the water is present at a beneficially "high" concentration level) operates at process temperatures of between around 0 degrees C to 10 degrees C and a pressure of about 150 psig. This is convenient to the implementation of the preferred embodiment since silica gel water loading capacity increases dramatically as the temperature of silica gel declines below about 25 degrees C.

A liquid sidestream is withdrawn from the midsection, and dried (preferably with silica gel) to form an essentially dry liquid sidestream; and the essentially dry liquid sidestream is reprocessed through the vinyl chloride monomer purification system and ultimately returned in the feed stream to the distillation column.

The silica gel is readily regenerated using EDC which is ramped from a temperatures of less than about 30 degrees C to a temperature of about 125 degrees C during the process of regeneration; this temperature range provides temperatures which are significantly lower than those required for molecular sieve regeneration, which typically uses hot inert gas at temperatures above 200 degrees C. Accordingly, the lower temperature provides some safety benefit in the use of silica gel when compared to molecular sieves. The silica gel is also more resistant to HCl attack and less prone to provide active sites for byproduct reactions than molecular sieves. These characteristics, when added to the lower required regeneration temperature, further indicate silica gel as the preferred drying agent since it is also a less reactive media as well as a safer (lower temperature of operation) media. The EDC used in the preferred embodiment is forwarded to an EDC manufacturing facility after use in regenerating the silica gel. In one embodiment, when relatively cool and also relatively hot EDC are available, use of both cold and hot EDC is advantageous in minimizing energy requirements in regeneration.

FIG. 1 shows a vinyl chloride monomer (VCM) purifying system 100 modified according to the present invention, in a preferred embodiment. Ethylene Dichloride (EDC) is fed to cracking furnace system 103 via line 101. Furnace product is conveyed via furnace output line 105 into primary distillation unit 107 which separates the furnace product feed into (a) a VCM and Hydrogen Chloride (HCl) overhead stream which is conveyed via line 109 into HCl distillation unit 115 and (b) a VCM and EDC bottoms stream which is conveyed via line 117 to EDC purification distillation unit 111. About 50% of the VCM fed to primary distillation unit 107 is further conveyed via line 109 with the other 50% being further conveyed via line 117.

EDC purification distillation unit 111 separates the VCM and EDC bottoms stream from primary distillation unit 107 into (a) purified EDC which exits via line 121 and (b) crude VCM which is conveyed via line 119 into VCM purification distillation unit 113. VCM purification distillation unit 113 separates crude VCM from EDC purification distillation unit 111 into (a) purified VCM which exits via line 129 and (b) lights which are conveyed via line 123 into HCl distillation unit 115.

In this regard, the composition of water in the midsection of the HCl/VCM distillation column measures between about 100 and 200 PPM water concentration when the feed stream (of vinyl chloride, HCl, and water) to the HCl/VCM distillation column demonstrates a water concentration of about 10 PPM during normal operation. The solubility limit of water in the material being processed at the usual operational conditions of the midsection of the HCl/VCM distillation column is between 50 and 200 ppm depending on the temperature, reflux, split in composition between HCl and VCM, and other tower operating parameters. It should be noted that, in a further surprising discovery respective to operation, a high reflux on the column beneficially increases midsection water composition for enabling mass transfer to a drying agent; accordingly, reflux is situationally used in water profile control. HCl distillation unit 115 is fed with both (a) the VCM and HCl overhead stream conveyed via line 109 and (b) lights conveyed via line 123. HCl distillation unit 115 separates its feed streams into (a) a crude HCl steam (containing any light impurities generated in cracking furnace system 103) which is conveyed via line 131 as recycle to an EDC manufacturing unit and (b) a VCM raffinate stream which is usually conveyed via line 125 as a second VCM product stream or which may optionally be returned to EDC purification distillation unit 111 for byproduct removal. The mid-section of HCl distillation unit 115 (where the water is present at a beneficially "high" concentration level for efficient drying purposes) operates at process temperatures of between around 0 degrees C to 10 degrees C at an operating pressure of about 150 psig. This is convenient to the implementation of the preferred embodiment using silica gel since silica gel water loading capacity increases dramatically as the temperature of silica gel declines below about 15 degrees C. Table 1 shows a representative profile of temperatures at various trays in one such HCl distillation unit 115.

TABLE 1

| HCl distillation unit 115 tray number | Tray temperature (degrees C) |
|---|---|
| 50 (top) | −30.7 |
| 42 | −30.0 |
| 38 | −24.0 |
| 30 | −7.4 |
| 23 | 2.8 |
| 21 | 3.4 |
| 19 | 14.1 |
| 17 | 46.1 |
| 13 | 61.5 |
| Bottoms | 61.6 |

The FIG. 1 depiction of vinyl chloride monomer (VCM) purifying system 100 does not show reflux lines, pumps, valves, instrumentation, safety relief and rupture devices, environmental safeguarding measures, and a control system which are generally used in the construction and operation of such unit operations and unified systems; except as further detailed herein, the incorporation, sizing, installation, and use of these components are apparent to those of skill.

A VCM side-draw is taken off of HCl distillation unit 115 via line 127, boosted with pump 175, and conveyed to dryers 133a,b. Dryer 133a has a bed of silica gel 157a, and dryer 133b has a bed of silica gel 157b. The VCM side-draw is sourced from any one of four take-offs (not shown) which connect to line 127 from trays twenty-two, twenty, seventeen and fifteen of HCl distillation unit 115 (HCl distillation unit 115 has fifty total trays). Normal VCM side-draw flow is usually about 0.25 kg/s, with a maximum VCM side-draw of about 1.0 kg/s, which represents a percentage of about 1.4% to 5.6% of the sum of the input from lines 109 and 123 to HCl distillation unit 115. In a preferred embodiment, sidedraw is effected as needed to control water consistent with stable operation of HCl distillation unit 115.

Restating the surprising discovery, it has been noted that the mid-section of an HCl distillation column, namely comprising from trays fifteen to twenty-two in a fifty-tray HCl distillation unit 115, accumulates the highest concentration of water in VCM purifying system 100. Accordingly, a side stream taken from this section of HCl distillation unit 115 has the most preferable mass transfer concentration gradient of water in VCM purifying system 100 when the mass transfer concentration gradient is defined respective to a water absorbent medium. As should be apparent, the vertical water profile in HCl distillation unit 115 shifts somewhat in operation with modifications in compositions of feed streams 109 and 123 and in general operating conditions with reflux effecting control of the water profile in the column.

Since the water accumulates to a high concentration at the mid-section, there are certain efficiencies in removing the water from the material at this particular point in the purifying process (i.e., it is essentially "easier" to remove water from about 150 PPM down to about 10 PPM by weight in the mid-section than it is to remove water from about 10 PPM down to about 1 PPM by weight in another stream). The cycle time of silica gel 157a,b is further improved dramatically when used to dry VCM side-stream from (e.g.) 150 PPM to 10 PPM instead of drying it from 10 PPM to 1 PPM since (a) silica gel loading capacity increases with inlet water concentration and (b) silica gel regeneration is facilitated with a higher acceptable residual post-regeneration water loading level in the dried silica gel in the 150 PPM to 10 PPM case.

Dryers 133a,b operate as a dual dryer set and as a virtual drying system process unit in the preferred embodiment—while one dryer (e.g. dryer 133a) is adsorbing water from the VCM side-draw stream of line 127, the other dryer (e.g. dryer 133b) is either in a regeneration procedure or in a waiting mode. Hence, water removal from HCl distillation unit 115 is continuously enabled.

The dried VCM side-draw stream of line 167 is returned to line 105. EDC is used in the preferred embodiment as the regeneration media for dryers 133a,b; in this regard, EDC is passed through a temperature profile of from less than 30 degrees C to about 125 degrees C in a regenerative cycle. Gradual temperature increases are required to (a) control the evolution of acid across the regenerative cycle and thereby (b) minimize the corrosive attributes of the discharged EDC and recycled water conveyed in line 135 to EDC manufacturing. In this regard, even as HCl is adsorbed along with water onto the silica gel during the drying operation, HCl and water in the silica gel are also desorbed from the silica gel during regeneration; this ongoing presence of both HCl and water creates a need for corrosion management in both the absorption and desorption operations. EDC temperature is adjusted (as further explained herein) in heating unit 161(a hot oil exchanger) prior to entry into either dryer 133a or dryer 133b in a time/temperature profile generally in accordance with that shown in FIG. 3.

The purpose of dryers 133a,b is to remove water from VCM purifying system 100. If not removed, water mixes with HCl in HCl distillation unit 115 to form a corrosive mixture; the corrosive mixture then reacts with iron and Monel in the unit to form corrosion products. These corrosion products accumulate on HCl distillation unit 115 trays and plug openings in those trays, deteriorating the operational characteristics of the unit. The accumulation of corrosion products eventually requires shutdown and cleaning of VCM purifying system 100, and such a shutdown represents a loss of productivity for the unit.

Dryers 133a and 133b, heating unit 161, analyzers 171 and 173 for water content analysis, and valves 139, 141, 143, 145, 147, 149, 151, and 153 function with lines 127, 137, 135, and 167 as a continuously operating drying system process unit two bed drying system which is managed as a drying system process unit for control purposes. While one dryer (e.g. dryer 133a) is absorbing water from VCM side-draw, the other dryer (e.g. dryer 133b) is either being regenerated and emptied or is in process wait mode. In the preferred embodiment, the maximum flow rate through dryers 133a,b is 2.0 kg/s, double the maximum side draw off of 1.0 kg/s so that both the maximum side draw from HCl distillation unit 115 and a return of any off-spec material can passed through the dryer prior to return to primary distillation unit 107 for reprocessing. Once a dryer has been regenerated, it remains idle until the on-line dryer becomes saturated with water. At this time, the VCM side-draw flow in line 127 is switched by use of valves 143, 145, 151 and 153 to the regenerated and waiting dryer. In facilitating measurements of real-time water composition in VCM side-draw and dried VCM side-draw, (a) a first water analyzer 171 is installed to measure the composition of water in VCM side-draw in line 127 and (b) a second water analyzer 173 is installed to measure the composition of water in dried VCM side-draw in line 167. Dryers 133a,b are each constructed of carbon steel; each has an internal volume of about 95 cubic feet, and each is loaded with 3900 pounds of silica gel 157a,b having a grade designation of 40.

Under normal operation, the dried VCM side-draw is discharged to line 105. However, after a dryer has become saturated, the VCM side-draw within it must be first drained at the beginning of the regeneration cycle. In this regard, the VCM side-draw is drained to a recycle tank (not shown) using a nitrogen purge as an assisting propellant and evaporative gas.

The discharged EDC from the regeneration process is recycled to an EDC manufacturing facility. VCM side-draw in line 127 typically has a temperature of between 0 and 10 degrees C and a composition of 80–92% VCM, 8–20% HCl, and 50 PPM–200 PPM water. The dried VCM side-draw leaving the discharge of dryer 133a,b is dried to no more than 50 PPM water in normal operation; when 50 PPM water is measured at the discharge, the bed is considered to be saturated and the VCM side-draw is switched to the other dryer. Line 109 has a flow of 16.5 kg/s, and a composition of (a) 73.5 mol %/62.0 mass % of HCl and (b) 26.5 mol %/38.0 mass % of VCM. Line 123 has a flow of 1.5 kg/s and a composition of (a) 4.0 mol %/6.7 mass % HCl and (b) 96 mol %/93.3 mass % VCM. Water overheads from HCl distillation unit 115 are less that 1 ppm and the VCM product specification (line 129) is for water at or below 50 ppm and for HCl at or below 0.2 ppm.

Figure 2:
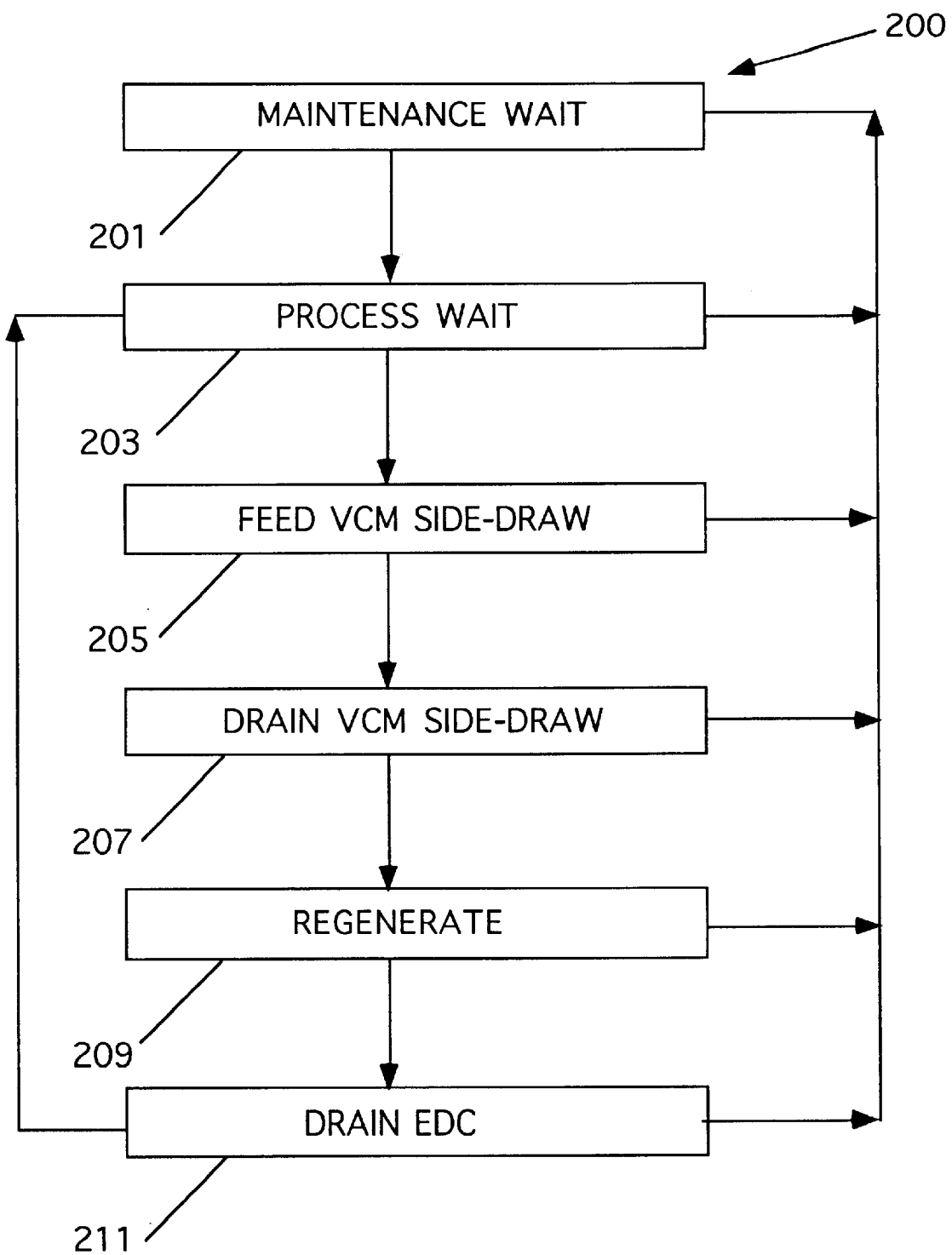
FIG. 2 outlines key process unit steps respective to the drying system process unit of FIG. 1.

In operation, a computerized control system is preferably used to control real-time configuration of VCM purifying system 100 for that portion of the system which is beneficially controlled via automation. In this regard, unit operations in dryers 133a and 133b, heating unit 161, analyzers 171 and 173, and valves 139, 141, 143, 145, 147, 149, 151, and 153 function with lines 127, 137, 135, and 167 as a continuously operating drying system process unit. FIG. 2 outlines the key process unit steps 200 respective to real-time operation of the drying system process unit as shown in part of FIG. 1. In this regard, FIG. 2 shows the key process unit steps 200 which apply to dryer 133a and dryer 133b individually; in this regard, dryer 133a is in only one process unit step of FIG. 2 at any particular moment, and dryer 133b is in only one process unit step of FIG. 2 at any particular moment. In collectively operating (a) dryers 133a and 133b, (b) heating unit 161, (c) analyzers 171 and 173, and (d) the valves (139, 141, 143, 145, 147, 149, 151, and 153) as a unified drying system process unit, actions in certain steps respective to one dryer respective to the application of the method of FIG. 2 will be conditional on the active step respective to the other dryer; for example, entry of dryer 133a into Regeneration Step 209 is normally not permitted if dryer 133b is not in Feed VCM Side-draw Step 205 because such a situation would deprive VCM purifying system 100 of use of the benefits of the drying system process unit.

Turning now to FIG. 2 and Maintenance Wait Step 201, valves (139, 141, 143, 145, 147, 149, 151, and 153) are closed, and pump 175 is off. Designation of the Maintenance Wait Step 201 as the active process unit step for real-time control coordination is usually entered (a) if the operating technician deems that the drying system process unit should halt its normal operational methodology for purposes related to repair or (b) if either HCl distillation unit 115, furnace system 103, or primary distillation unit 107 are recognized by the control system as in a mode establishing an unsuitable basis for continued operation of the drying system process unit.

In the Process Wait Step 203 for dryer 133b, valves 141, 143, 149, and 153 are all closed. In the Process Wait Step 203 for dryer 133a, valves 139, 145, 147, and 151 are all closed.

When HCl distillation unit 115, cracking furnace system 103, and primary distillation unit 107 are functioning in a stable operational mode in real-time and temperature measurements (not shown) of the dryer are verified to be below 25 degrees C, the process control system (a) defines the status of dryer 133a as being in Feed VCM side-draw Step 205 and (b) opens valves 145 and 151. The control system energizes pump 175 and flow is forwarded to dryer 133a until water analyzer 173 detects a high reading. An example of performance data in Feed VCM side-draw Step 205 is shown in Table 2. Table 2 shows pilot plant drying data for VCM side draw taken from HCl distillation unit 115 over a period of four days. Data in Table 2 demonstrates removal of a large differential concentration of water from the HCl/VCM mixture for an extended period of time, with water concentration in dryer discharge being maintained below the saturation limit of 50 ppm (in respect to the highly corrosive aqueous HCl phase).

Another performance statistic apparent in the data is that silica gel is capable of a substantial weight % loading with water. Note that the silica gel was loaded to 6.2% water on the third day of operation.

TABLE 2

| Day | Online Time (hours) | Flow-rate (1 ph) | HCl col mid-section $H_2O$ (ppm w/w) | HCl col bottom water (ppm w/w) | Dried VCM (ppm w/w) | HCl wt % | Water loaded gms | Accumulated water loaded (gms) | Accumulated wt % loaded | % water removed |
|---|---|---|---|---|---|---|---|---|---|---|
| Day 1 | 2.5 | 4.0 | 130.3 | 8.2 | 13.4 | 8.1 | 1.1 | 1.1 | 0.3 | 89.7 |
| Day 2 | 24.0 | 4.0 | 164.3 | 8.7 | 29.5 |  | 10.7 | 11.7 | 3.2 | 82.0 |

TABLE 2-continued

| Day | Online Time (hours) | Flow-rate (1 ph) | HCl col mid-section H₂O (ppm w/w) | HCl col bottom water (ppm w/w) | Dried VCM (ppm w/w) | HCl wt % | Water loaded gms | Accumulated water loaded (gms) | Accumulated wt % loaded | % water removed |
|---|---|---|---|---|---|---|---|---|---|---|
| Day 3 | 48.0 | 4.0 | 172.3 | 15.1 | 48.5 | 8.1 | 10.9 | 22.7 | 6.2 | 71.9 |
| Day 4 | 75.0 | 4.0 | 108.0 | 7.7 | 59.7 | 7.3 | 4.8 | 27.5 | 7.5 | 44.8 |

When a high reading in analyzer 173 (above 50 PPM) in Feed VCM side-draw Step 205 is measured by the process control system, the process control system defines the status of dryer 133b as being in Feed VCM side-draw Step 205 and opens valves 143 and 153 to enable flow through dryer 133b. The process control system then (a) defines the status of dryer 133a as being in Drain VCM side-draw Step 207, (b) closes valves 145 and 151, and (c) opens a drain valve (not shown) and activates a nitrogen purge (not shown) to enable VCM side-draw to drain from dryer 133a into a recycle tank (not shown) until a low level switch (not shown) in dryer 133a indicates that dryer 133a is essentially emptied of VCM side-draw. When the low level switch activates, the nitrogen purge is discontinued and the drain valve is closed. The recycle tank is periodically recycled into purifying system 100.

Figure 3:
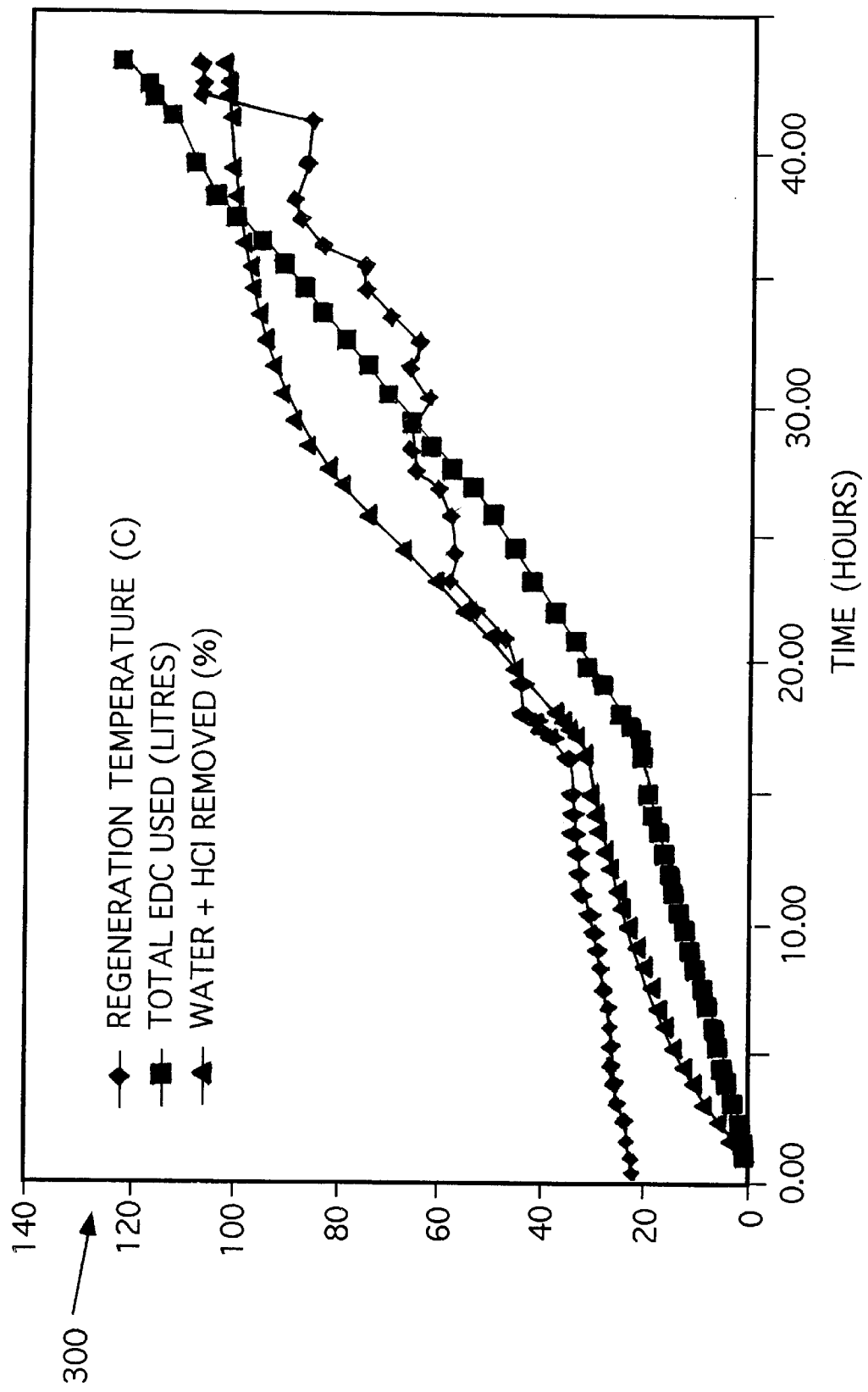
FIG. 3 shows pilot plant data for a silica gel regeneration instance.

When the low level switch in dryer 133a indicates that VCM side-draw has been emptied, the process control system defines the status of dryer 133a as being in Regeneration Step 209 and opens valves 139 and 147 to convey EDC through dryer 133a. Heating unit 161 is controlled to provide EDC at a temperature profile as shown in FIG. 3. Essentially, heating unit 161 begins at a temperature of less than 30 degrees C and then ramps the temperature of the EDC up at a rate of about 2 degrees C per hour until a temperature of 125 degrees C is attained.

FIG. 3 illustrates the temperature ramping process by showing pilot plant data for a silica gel 157a,b regeneration instance. The silica gel 157a,b was loaded with water to a weight percentage of 13.5% by drying VCM side-draw from HCl distillation unit 115. A loading of 11.6% HCl was also measured in the gel. FIG. 3 shows the regeneration temperature used over a 45 hour period, the rate of water and HCl removal from the gel, and the amount of EDC used.

Returning to FIG. 2, after executing completion of the temperature profile in regeneration Step 209, the process control system (a) defines the status of dryer 133a as being in Drain EDC Step 211, (b) closes valves 147 and 139, and (c) opens a drain valve (not shown) to enable EDC to drain from dryer 133a into the recycle tank (not shown) until the low level switch (not shown) in dryer 133a indicates that dryer 133a is essentially emptied of EDC.

When the low level switch in dryer 133a indicates that dryer 133a is essentially emptied of EDC, the process control system then defines the status of dryer 133a as being in Process Wait Step 203.

As should be appreciated by those of skill, dryer 133a can be substituted for dryer 133b and dryer 133b can be substituted for dryer 133a in the foregoing discussion respective to FIG. 2 (with valves 143, 141, 149, and 153 also being mutually cross-substituted with valves 145, 139, 147, and 151) to describe complementary operation of the dryers in the case where dryer 133b is regenerated. As each dryer (133a, 133b) is directed by the process control system through its operational procedure according to method 200, the drying system process unit provides a continuous water removal subsystem within VCM purifying system 100 for treating water rich VCM side-draw taken from HCl distillation unit 115. In the course of real-time operation, dryer 133a and dryer 133b alternatively act as the "on-line" dryer in VCM purifying system 100.

The present invention has been described in an illustrative manner. In this regard, it is evident that those skilled in the art, once given he benefit of the foregoing disclosure, may now make modifications to the specific embodiments described herein without departing from the spirit of the present invention. Such modifications are to be considered within the scope of the present invention which is limited solely by the scope and spirit of the appended claims.

We claim:

1. A method of removing water in a vinyl chloride monomer purification system, comprising the steps of:
   providing a distillation column for separation of a liquid admixture of vinyl chloride, hydrogen chloride, and water into an essentially pure vinyl chloride product stream and a hydrogen chloride distillate stream, said distillation column having a top, a bottom, and a midsection; and
   placing a drying system in fluid communication with said midsection where the water is at sufficient concentration to provide a useful mass transfer flux of water from a withdrawn midsection stream into a drying agent.

2. A method, in a vinyl chloride monomer purification system, of removing water from a distillation column separating vinyl chloride, hydrogen chloride, and water into an essentially pure vinyl chloride product stream and a hydrogen chloride distillate stream, said distillation column having a top, a bottom, and a midsection comprising the steps of:
   withdrawing a liquid sidestream from said midsection;
   drying said liquid sidestream to form an essentially dry liquid sidestream; and
   reprocessing said dry liquid sidestream through said vinyl chloride monomer purification system.

3. Removing water from an admixture of vinyl chloride, hydrogen chloride, and water by drying a sidestream drawn from the midsection of a distillation column separating said hydrogen chloride from said vinyl chloride.

4. The method of any of claims 2 to 3 wherein said midsection is defined as that portion of the distillation column having an operating temperature between about 0 degrees C and about 10 degrees C.

5. The method of any of claims 2 to 3 wherein said drying further comprises using silica gel desiccant as a drying agent.

6. The method of claim 1 wherein said midsection is defined as that portion of the distillation column having an operating temperature between about 0 degrees C and about 10 degrees C and said drying system further comprises a silica gel desiccant for drying said liquid sidestream.

7. The method of claim 5 further comprising the step of regenerating said silica gel desiccant with ethylene dichloride.

8. The method of claim 6 wherein said drying system has a regeneration system for providing ethylene dichloride to regenerate said silica gel desiccant.

* * * * *